United States Patent [19]

Saito et al.

[11] Patent Number: 4,850,004
[45] Date of Patent: Jul. 18, 1989

[54] METHOD AND SYSTEM FOR ACQUIRING COMPUTERIZED TOMOGRAM DATA

[75] Inventors: Yasuo Saito, Tochigi-Ken; Yasuo Nobuta, Ootawara, both of Japan

[73] Assignee: Kabushiki Kaisha Toshiba, Kawasaki, Japan

[21] Appl. No.: 178,004

[22] Filed: Apr. 5, 1988

[30] Foreign Application Priority Data

Apr. 10, 1987 [JP] Japan .................................. 62-89591

[51] Int. Cl.$^4$ ............................................. G06F 15/42
[52] U.S. Cl. ........................................ 378/4; 378/14; 378/19; 378/901
[58] Field of Search ................... 378/4, 11, 13, 14, 15, 378/19, 114, 116, 901; 250/363.02; 364/413.14, 413.15

[56] References Cited

U.S. PATENT DOCUMENTS 4,097,744  6/1978  LeMay ................................. 378/14
4,580,219  4/1986  Pelc et al. ........................... 378/901

*Primary Examiner*—Carolyn E. Fields
*Assistant Examiner*—David P. Poite
*Attorney, Agent, or Firm*—Finnegan, Henderson, Farabow, Garrett, & Dunner

[57] ABSTRACT

In computerized tomography apparatus having a radiation source and a detector, when the radiation source and the detector are rotated in a rotational direction, acquisition of computerized tomogram data takes place in accordance with a data acquiring direction. When the radiation source and the detector are rotated in a rotational direction opposite to the rotational direction, acquisition of the computerized tomogram data is also performed from a data acquiring direction opposite to the data acquisition direction, thereby agreeing with the position of imaginary source. The position of imaginary source is near a subject than that of the radiation source, so that a high resolution is obtained.

8 Claims, 6 Drawing Sheets

METHOD AND SYSTEM FOR ACQUIRING COMPUTERIZED TOMOGRAM DATA

BACKGROUND OF THE INVENTION

1. Field of the Invention

This invention relates to a method and system for acquiring CT data by using continuous radiation in a CT apparatus.

2. Description of the Related Art

In the case of a conventional CT (computerized tomography) apparatus, an X-ray source generating a fan beam and an X-ray detector having channels opposite to the X-ray source are rotated in unison around a subject under examination so as to acquire X-ray data transmitted through the object. The following are methods of acquiring X-ray data from one fan beam:

(1) The X-ray data is simultaneously acquired by all the channels of the X-ray detector, and the data acquired by the respective channels is transferred, in sequential fashion, to a data processor.

(2) The channels of the X-ray detector are operated on a time-division basis to sequentially acquire the X-ray data, the X-ray data acquired by each channel being transferred to the data processor immediately upon acquisition.

In the case of the first method, when the X-ray data is acquired by continuous emission of X-rays, an additional period of time from the completion of data acquisition until the completion of data transfer is required for all the channels of the detector. Moreover, since the continuous X-ray is used, X-ray transmitted during the additional period of time becomes useless.

With the second method, on the other hand, since the timing of X-ray data acquisition varies with the channels of the detector, the following problems will arise.

For example, as is shown in FIG. 1A, when X-ray source 1 and X-ray detector 4, which has channels opposite to source 1, are rotated in direction 3a, with the center 2 of object P as the axis of rotation—in other words, while X-ray source 1 generating an X-ray fan beam is moved from a position 1a to a position 1b—X-ray detector 4 acquires X-ray data, in sequential fashion, from the data of first channel 4b, corresponding to X-ray pass 7, to the data of 512th channel 4a, corresponding to X-ray pass 8a, along the data acquiring direction 6 (refer to FIG. 2). This corresponds to the case where data is acquired on the basis of a fan beam transmitted from an intersectional point 9 (imaginary point) of the X-ray passes, the position of such an imaginary point 9 being closer to object P than the actual position 1a or 1b of source 1.

When, on the other hand, source 1 is rotated in the opposite direction 3b, as is shown in FIG. 1B, data is acquired sequentially along direction 6, from first channel 4b corresponding to X-ray pass 7 of source 1 at position 1a, to 512th channel 4a corresponding to X-ray pass 8b of source 1 at position 1c. In this case, intersectional point 10 (the imaginary point of this case) of X-ray passes 7 and 8b is located outside the actual position 1a or 1c of source 1 with respect to object P.

As described above, when the data acquiring direction is constant regardless of the rotational direction of the source, data based on different scaling factors will be acquired because the position of the imaginary source varies by directions of rotation of the actual source. Thus, in reconstructing a CT image, various parameters which would be affected by different scaling factors must be adjusted so as to correct the data obtained. When data correction is performed by computer processing, however, problems will arise in the processing period of time, the memory capacity for data, etc.

Therefore, it is desired to acquire CT data so as to reconstruct CT images without data correction due to different scaling factors.

SUMMARY OF THE INVENTION

An object of this invention is to provide a method and system for acquiring CT data without data correction of different scaling factors for the rotational direction of an X-ray source arranged in a CT apparatus.

According to the present invention, there is provided a method for acquiring computerized tomogram data of a subject by using a radiation source and a detector with channels, incorporated in a computerized tomography apparatus, the method comprising the steps of: switching a rotational direction of the radiation source, switching a data acquiring direction of the detector by switching the rotational direction of the radiation source, and acquiring the computerized tomogram data of the subject, in accordance with the switched data acquiring direction of the detector.

According to the present invention, there is provided a system for acquiring computerized tomogram data of a subject by using a radiation source and a detector with channels, incorporated in a computerized tomography apparatus, the system comprising: first switching means for switching a rotational direction of the radiation source; second switching means for switching a data acquiring direction of the detector by the rotational direction of the radiation source switched by the first switching means; and, means for acquiring the computerized tomogram data of the subject, in accordance with the data acquiring direction of the detector switched by the second switching means.

DETAILED DESCRIPTION OF THE PREFERRED EMBODIMENT

An embodiment of the present invention will be described with reference to the accompanying drawings.

Figures 1A, 1B:
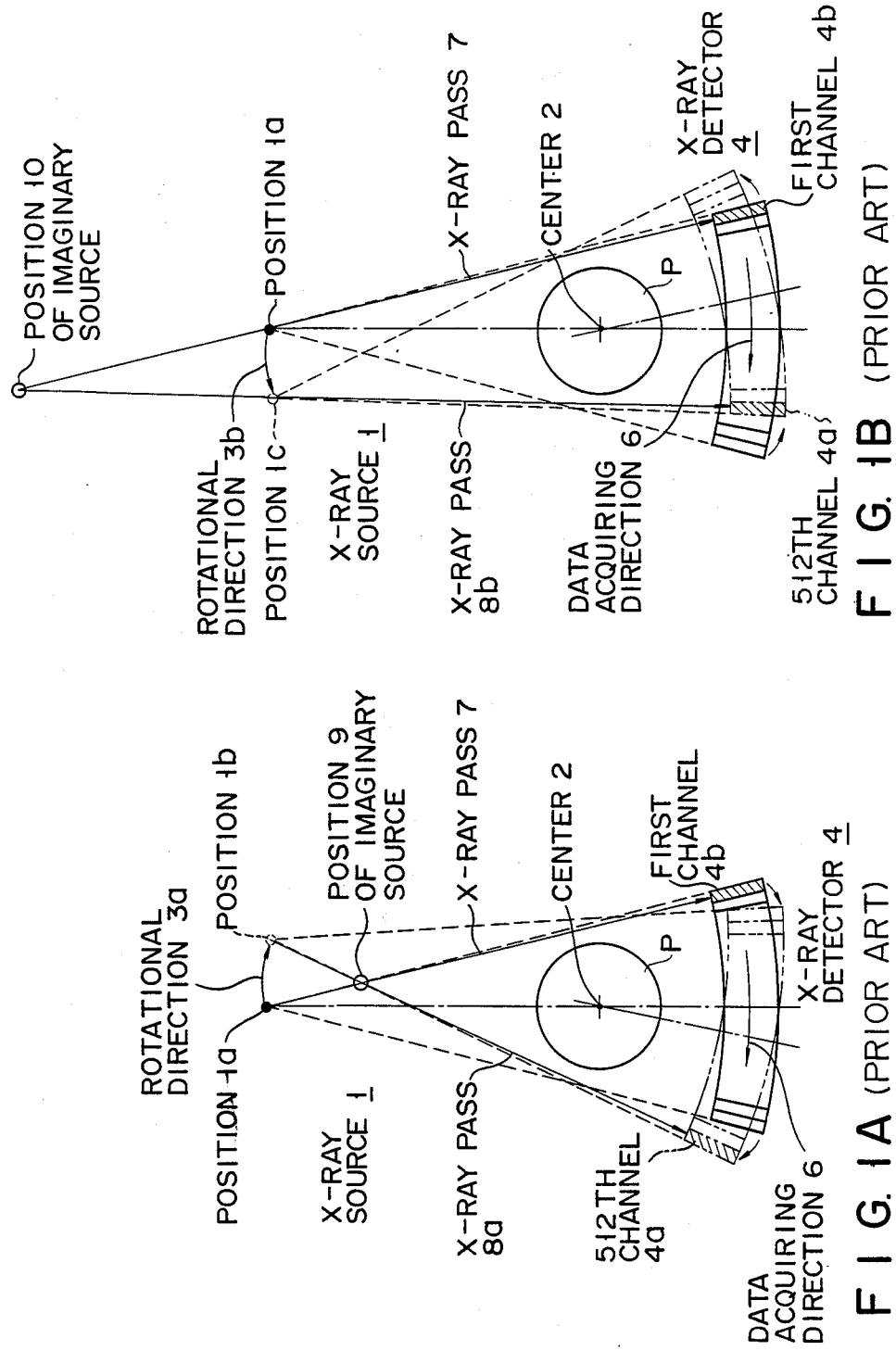
FIGS. 1A and 1B are views for explaining the conventional operations in CT data acquisition.
Figure 2:
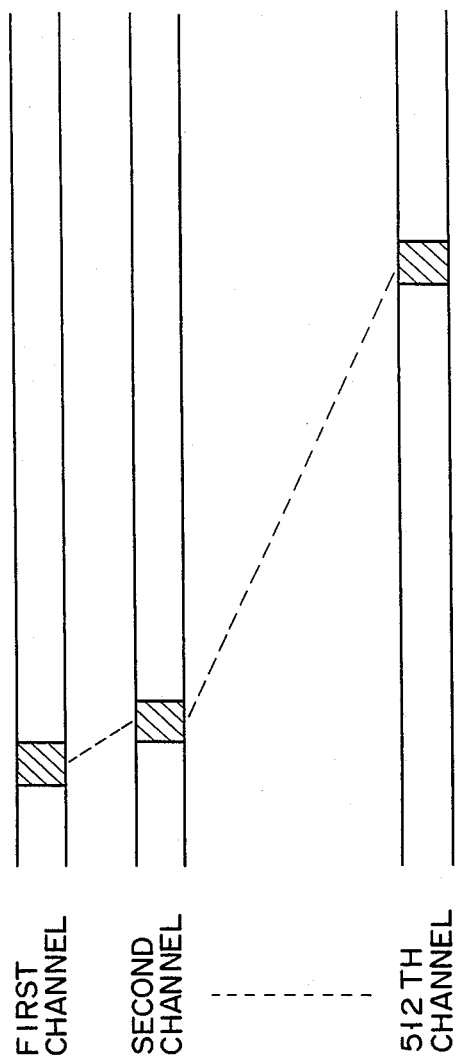
FIG. 2 is a timing chart of the conventional CT data acquisition.
Figure 3:
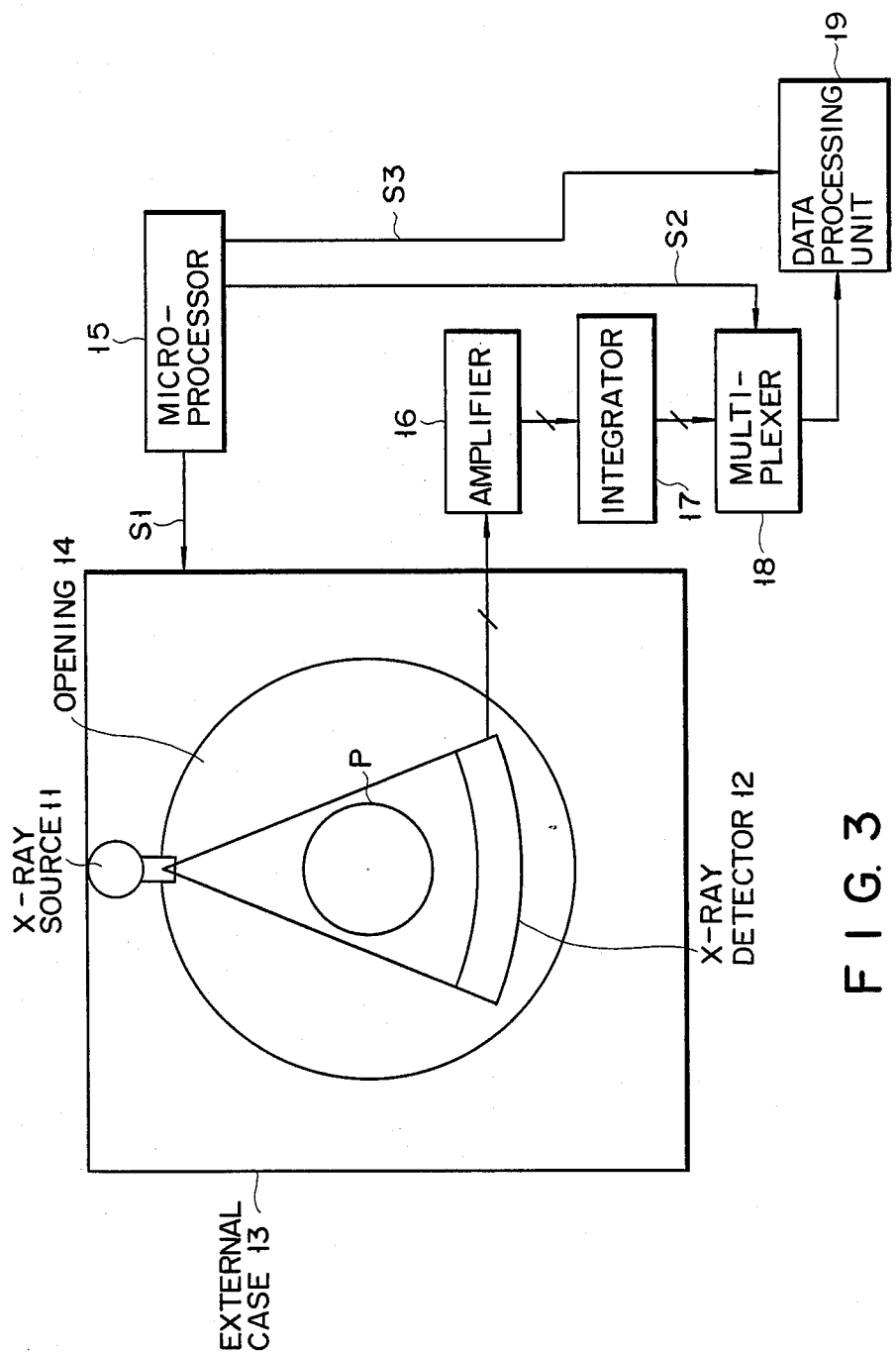
FIG. 3 shows an arrangement of a CT data acquisition system.

Referring now to FIG. 3, external case 13 is provided with opening 14 into which object P under examination is inserted. X-ray source 11 and X-ray detector 12 are disposed in external case 13 such that they oppose to each other with object P interposed therebetween and can be rotated around object P by a motor and a motor driving circuit not shown.

Data obtained by X-ray detector 12 is amplified in amplifier 16, integrated in integrator 17, and then input via multiplexer 18 into data processing unit 19. Data processing unit 19 comprises an analog-to-digital (A/D) converter (not shown), and reconstructs a CT image by using the digital data converted by A/D converter. Microprocessor 15 supplies signal S1 for specifying a rotational direction of X-ray source 11 and X-ray detector 12 disposed within external case 13, signal S2 for specifying direction of data acquisition in the plurality of channels of X-ray detector 12, and signal S3 for CT image reconstruction processing by data obtained by X-ray detector 12.

Figure 4:
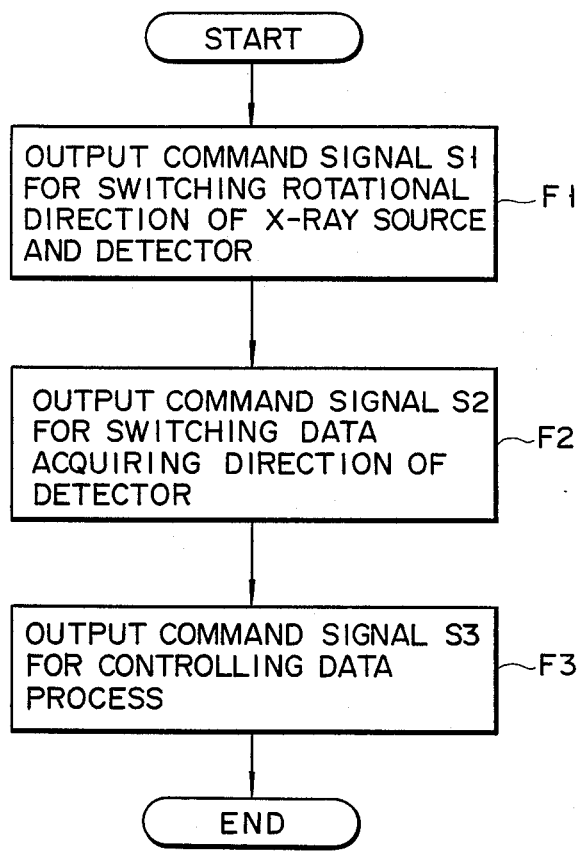
FIG. 4 is a flowchart showing an operation of the microprocessor in the CT data acquisition system.

Referring to a flowchart of FIG. 4, the operation of microprocessor 15 will be described hereinafter. In step F1 microprocessor 15 supplies command signal S1 to the motor driving circuit for switching the rotational direction of X-ray source 11 and X-ray detector 12.

In step F2 microprocessor 15 supplies command signal S2 to multiplexer 18 so that the data acquiring direction in the channels of X-ray detector 12 coincides with the rotational direction of X-ray source 11 and X-ray detector 12 which is switched by command signal S1 supplied in step F1. The data acquisition is started by steps F1 and F2. In step F3 command signal S3 is supplied to data processing unit 19 so that a CT image is reconstructed by acquired data.

Next, with reference to FIGS. 5A and 5B, and FIGS. 6A and 6B the operation of the system will be described.

Figures 5A, 5B:
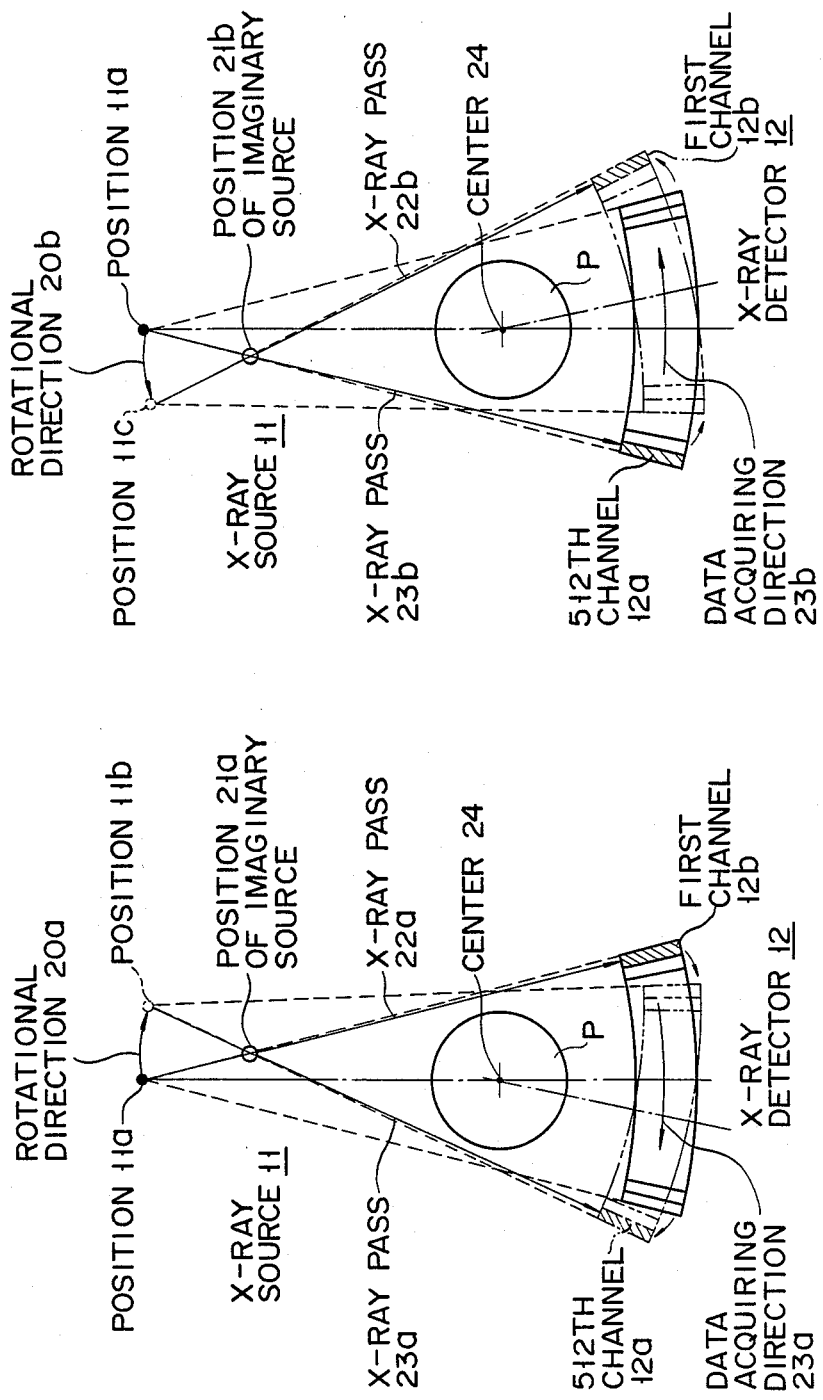
FIGS. 5A and 5B are views showing the operation of CT data acquisition according to an embodiment of this invention.
Figures 6A, 6B:
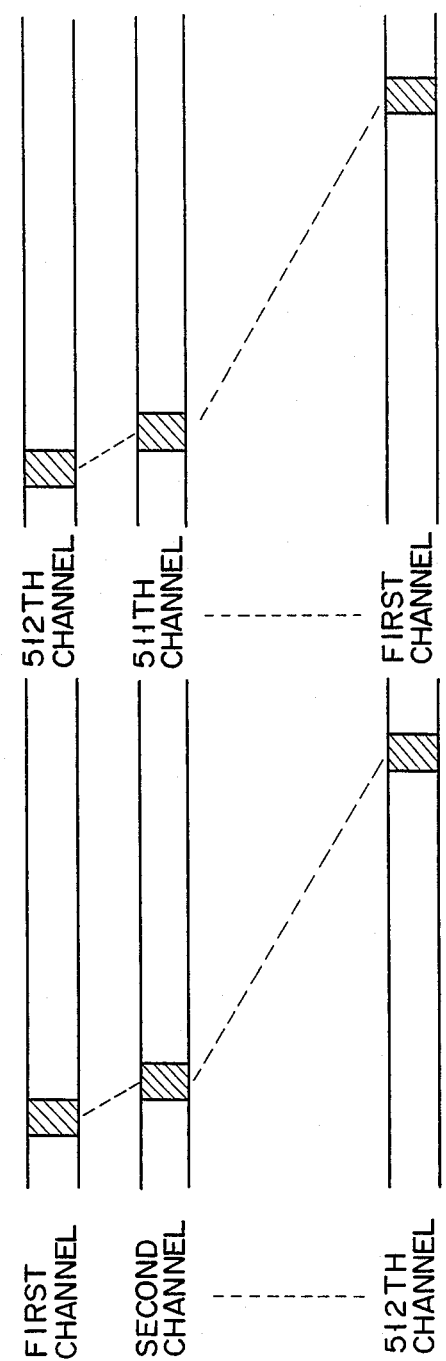
FIGS. 6A and 6B are timing charts of CT data acquisition in the embodiment of this invention.

As shown in FIG. 5A, where X-ray source 11 and X-ray detector 12 having 512 channels are rotated in direction 20a, in other words, while source 11 moves from position 11a to position 11b, the data acquisition for one fan beam is performed in sequence from first channel 12b to 512th channel 12a as shown in FIG. 6A. More specifically, X-ray detector 12 acquires the data in first channel 12b for X-ray pass 22a first, data in turn along the same direction as rotational direction 20a of X-ray source 11 and X-ray detector 12, and finally the data in 512th channel 12a for X-ray pass 23a. As a result, the data based on a fan beam from intersection 21a (imaginary point) of the X-ray passes is acquired. Noted that X-ray source 11 and X-ray detector 12 rotate taking the center 24 of object P as axis of rotation.

In order to arrange a cable connected to rotation circuit of CT apparatus, where data is acquired by rotating X-ray source 11 and X-ray detector 12 in rotational direction 20b (FIG. 5B), microprocessor 15 supplies signal S2 for switching the data acquiring direction 23b of X-ray detector 12 to coincide with the rotational direction 20b of X-ray source 11 and X-ray detector 12. That is, data is acquired sequentially from 512th channel 12a to first channel 12b as shown in FIG. 6B. Noted that the data in 512th channel 12a is based on X-ray pass 23b from source 11 at position 11a, and the data in first channel 12b on X-ray pass 22b from source 11 at position 11c. As a result, the intersection 21b of the X-ray passes in FIG. 5B and the intersection 21a in FIG. 5A are on concentric circles. Namely, the position of the imaginary source of the fan beam in this case coincides with that of FIG. 5A regardless of the rotational direction of the X-ray source and the X-ray detector. In addition, the position 21b of the imaginary source is closer to object P than the actual position 11a or 11b of the X-ray source.

As described above, since the positions of the imaginary source in the data acquisition coincide with each other regardless of the rotational direction of the X-ray source and the X-ray detector, no correction for the scaling factor is needed in the CT image reconstruction, and high-speed processing and reduction in memory capacity can be achieved. Further, since the position of the imaginary source in the data acquisition exists closer to the object than the actual position of the X-ray source, an improvement in resolution can be obtained.

The present invention is not limited to the above embodiment, and various changes and modifications can be made within the spirit and scope of this invention.

What is claimed is:

1. A method for acquiring computerized tomogram data of a subject by using a radiation source and a detector with channels, incorporated in a computerized tomography apparatus, the method comprising the steps of:
   switching a rotational direction of the radiation source and the detector;
   switching a data acquiring direction of the detector by switching the rotational direction of the radiation source; and,
   acquiring the computerized tomogram data of the subject in accordance with the switched data acquiring direction of the detector.

2. A method according to claim 1, wherein acquisition of the computerized tomogram data is performed from end to end of the channels arranged in the detector.

3. A method according to claim 1, wherein the step of switching the data acquiring direction of the detector comprises a step of selecting the data acquiring direction of the detector so as to be in agreement between the rotational direction of the detector and the rotational direction of the radiation source.

4. A method according to claim 3, wherein acquisition of the computerized tomogram data is performed from end to end of the channels arranged in the detector.

5. A system for acquiring computerized tomogram data of a subject by using a radiation source and a detector with channels, incorporated in a computerized tomography apparatus, the system comprising:
   first switching means for switching a rotational direction of the radiation source and the detector;
   second switching means for switching a data acquiring direction of the detector by the rotational direction of the radiation source switched by the first switching means; and,
   means for acquiring the computerized tomogram data of the subject, in accordance with the data acquiring direction of the detector switched by the second switching means.

6. A system according to claim 5, wherein acquisition of the computerized tomogram data is performed from end to end of the channels arranged in the detector.

7. A system according to claim 5, wherein the second switching means comprises means for selecting the data acquiring direction of the detector so as to be in agreement between the rotational direction of the detector and the rotational direction of the source.

8. A system according to claim 7, wherein acquisition of the computerized tomogram data is performed from end to end of the channels arranged in the detector.

* * * * *